United States Patent [19]

Wu et al.

[11] 4,321,365

[45] Mar. 23, 1982

[54] OLIGONUCLEOTIDES USEFUL AS ADAPTORS IN DNA CLONING, ADAPTED DNA MOLECULES, AND METHODS OF PREPARING ADAPTORS AND ADAPTED MOLECULES

[75] Inventors: Ray J. Wu, Ithaca, N.Y.; Chander P. Bahl, Concord, Calif.; Saran A. Narang, Ottawa, Canada

[73] Assignee: Research Corporation, New York, N.Y.

[21] Appl. No.: 843,422

[22] Filed: Oct. 19, 1977

[51] Int. Cl.$^3$ .............................................. C07H 21/04
[52] U.S. Cl. ...................................... 536/27; 536/28; 536/29
[58] Field of Search ................................ 536/26-29; 435/317, 172

[56] References Cited

U.S. PATENT DOCUMENTS 4,237,224  12/1980  Cohen et al. ..................... 435/172

OTHER PUBLICATIONS

Marians et al., Nature, vol. 263, pp. 744–748 (1976).
Heyneker et al., Nature, vol. 263, pp. 748–752 (1976).
Scheller et al., Science, vol. 196, pp. 177–180 (1977).
Bahl et al., Gene 1, 81–92 (1976).
Pribnow, Proc. Nat. Acad. Sci., vol. 72, pp. 784–788, 1975.
Polisky et al., Proc. Nat. Acad. Sci., vol. 73, pp. 3900–3905 (1976).
Itakura et al., Science, vol. 198, pp. 1056–1066 (1977).

*Primary Examiner*—Blondel Hazel
*Attorney, Agent, or Firm*—Cooper, Dunham, Clark, Griffin & Moran

[57] ABSTRACT

Synthetic oligonucleotides have been designed and prepared which are useful in the molecular cloning of a variety of DNA molecules. By means of such oligonucleotides, genetic informational material, e.g., DNA, can be joined to a cloning vehicle and transferred into host cells by transformation. Additionally, a method for determining whether genetic informational material has been transferred into transformed host cells has been developed.

19 Claims, No Drawings

OLIGONUCLEOTIDES USEFUL AS ADAPTORS IN DNA CLONING, ADAPTED DNA MOLECULES, AND METHODS OF PREPARING ADAPTORS AND ADAPTED MOLECULES

The invention described herein was made in the course of work under a grant, GM-18887, from the Department of Health, Education and Welfare.

BACKGROUND OF THE INVENTION

Molecular cloning has become a powerful tool for the amplification of specific DNA (deoxyribonucleic acid) fragments and their subsequent isolation in high yields. Two basic steps are involved in molecular cloning. First the DNA fragments to be cloned are joined in vitro to an autonomously replicating cloning vehicle molecule, e.g., plasmid DNA [Cohen, S. N. et al., PNAS 70, 3240 (1973); Tanaka, T. and Weisblum, B., J. Bacteriology 121, 354 (1975)] or λ phage DNA [Thomas, M. et al., PNAS 71, 4579 (1974); Murray, N. E. and Murray, K., Nature 251, 476 (1974)]. The hybrid recombinant DNA-cloning vehicles so formed are then introduced into host cells, e.g., E. coli cells, by transformation and cloned by a suitable technique such as single colony isolation or plaque formation.

In one cloning method, two different DNA molecules are cut by the same restriction endonuclease to produce identical cohesive ends. The DNA molecules are annealed to one another and then covalently joined by DNA ligase. This method limits the size and kind of DNA fragments that can be cloned since it often requires cloning of a much larger DNA fragment that one is inserted in. For example, if one wants to clone a small DNA fragment such as a promoter (e.g., an RNA polymerase protected fragment), the nearest restriction endonuclease sites may be relatively distant, and thus extraneous DNA sequences must be included in the cloned DNA. This creates the possibility that undesirable or even hazardous sequences may be transferred, and it is this possibility which has led to public interest in the entire area of molecular cloning and recombinant DNA research. Furthermore, many DNA fragments cannot be cloned by this method because of the lack of a suitable restriction enzyme for producing molecules with appropriate cohesive ends.

The present invention utilizes chemically synthesized oligonucleotides having nucleotide sequences which are the recognition sites for restriction endonucleases as adaptor molecules. These adaptor molecules are joined at the ends of natural or synthetic DNA molecules to form adapted DNA molecules. The ends of such natural or synthetic DNA molecules can be even-ended or can have a protruding nucleotide sequence. Alternatively, adapted DNA molecules which comprise synthetic DNA molecules having such adaptor molecules incorporated therein at their ends are prepared. Such adapted DNA molecules are then joined to a cloning vehicle, thereby making the cloning procedure much more selective, versatile and safe. A part of the substance of this invention has been described recently in two publications (Bahl, Chander P., et al., Gene 1, 81 (1976) and Marians, K. J. et al., Nature, 263, 744 (1976)]. These publications are hereby incorporated into the present disclosure and made part thereof.

BRIEF SUMMARY OF THE INVENTION

This invention concerns a novel approach to the molecular cloning of a variety of DNA molecules. In one aspect of the invention, adaptor molecules useful for the insertion of genetic informational material, e.g., DNA, into a cloning vehicle have been defined and methods of preparing such adaptor molecules have been developed. In another aspect of the invention, adapted DNA molecules have been defined which comprise genetic informational material, e.g., DNA, for insertion into a cloning vehicle and adaptor molecules joined at both ends to the genetic informational material being inserted. Methods of preparing such adapted DNA molecules have also been developed. In still another aspect of the invention, modified cloning vehicles which contain such adapted DNA molecules have been defined and a method of preparing such modified cloning vehicles has been developed. In yet another aspect of the invention, such modified cloning vehicles are used to transform host cells and thus transfer genetic informational material such as DNA into host cells. Finally, the invention describes a method for determining whether genetic informational material has been transferred into cells by using an indicator DNA such as the lac operator as part of the genetic informational material in an adapted DNA molecule, forming a modified cloning vehicle which includes such an adapted DNA molecule, transforming the host cells using the modified cloning vehicle and screening the transformed cells to determine whether transfer has taken place.

These and other aspects of the invention are set forth more fully in the detailed description of the invention and the claims which follow.

DETAILED DESCRIPTION OF THE INVENTION

Adaptor Molecules

Adaptor molecules for the insertion of genetic informational material, e.g., DNA, into cloning vehicles have been prepared. These adaptor molecules are either single-stranded or double-stranded oligonucleotides. If double-stranded, adaptor molecules may have either one protruding nucleotide sequence which is a recognition site for a restriction endonuclease at one end of the duplex or two protruding nucleotide sequences which are recognition sites for the same or different restriction endonucleases at opposite ends of the duplex.

Examples of protruding nucleotide sequences which are recognition sites for restriction enzymes include: 5' pA-A-T-T, the partial recognition site for EcoRI restriction endonuclease; 5' pG-A-T-C, the partial recognition site for BamI restriction endonuclease; and 5' pA-G-C-T, the partial recognition site for HindIII restriction endonuclease. Similar adaptor molecules with partial recognition sites for other restrictions endonucleases such as PstI, SalI, HaeII, XmaI and BglII can also be synthesized and used for cloning.

The adaptor molecules of the invention are prepared in a number of ways. First, duplex adaptor molecules having one protruding nucleotide sequence may be prepared by chemically synthesizing single-stranded oligonucleotides which include the recognition site for a restriction endonuclease and which are self-complementary. A double-stranded duplex is then prepared from the self-complementary oligonucleotides and the duplex is then contacted with the restriction endonuclease whose recognition site is included in the oligonucleotides. The restriction endonuclease digests the duplex in such a way that an adaptor molecule having a protruding nucleotide sequence which is the recognition site for the restriction endonuclease results.

For example, two self-complementary decadeoxyribonucleotides d(C-C-G-G-A-T-C-C-G-G) (BamI adaptor sequence including the BamI restriction endonuclease recognition site, 5' pG-G-A-T-C-C) and d(A-C-A-A-G-C-T-T-G-T) (HindIII adaptor sequence including the HindIII restriction endonuclease recognition site, 5' pA-A-G-C-T-T) were synthesized by the improved phosphotriester method developed previously [Itakura, K. et al., *Canadian J. Chem.* 51, 3649 (1973); Itakura, K. et al., *J. Am. Chem. Soc.* 97, 7327 (1975); Katagiri, N. et al., *J. Am. Chem. Soc.* 97, 7332 (1975); Bahl, C. P., et al., *Gene* 1, 81 (1976); Stawinsky, J., et al., *Nucleic Acids Res.* 4, 353 (1977)]. Two new steps were introduced in these syntheses: the dimethoxytrityl group was removed by a 2% solution of benzenesulfonic acid in chloroform and the chlorophenyl phosphate protecting group was removed by treatment with concentrated ammonium hydroxide for 4–6 hours. The oligonucleotides were characterized by two-dimensional electrophoresis-homochromatography of their partial venom phosphodiesterase digestion products [Jay, E., et al., *Nucleic Acids Res.* 1, 331 (1974) and Tu, C. D., et al., *Anal. Biochem* 74, 73 (1976)] which verified the above sequences of the two synthetic decadeoxynucleotides.

Double-stranded duplexes were prepared from these two self-complementary oligonucleotides. Specifically, the chemically synthesized decadeoxynucleotides (400 pmoles) were phosphorylated at the 5' end using [γ³²P] ATP and polynucleotide kinase [Wu, R. et al., *Methods in Cancer Res.,* 12, 88 (1976)]. The labeled decadeoxynucleotides were dissolved in a suitable amount (about 100 μl) of a suitable buffer such as 100 mM Tris-HCl (pH 7.5) heated to about 90° C. for about 1 minute, quickly chilled to about 0° C. and then incubated at about 70° C. for about 30 minutes. The duplexes of the decadeoxynucleotides were formed by slowly cooling the samples to about room temperature and then to about 4° C.

The duplex which included the recognition site for BamI restriction endonuclease was then contacted with this enzyme [Wilson, G. A. and Young, F. E., *J. Mol. Biol.* 97, 123 (1975)] and after digestion gave an adaptor molecule having the protruding sequence 5' pG-A-T-C. Thus,

```
5' pC—C—G—G—A—T—C—C—G—G
3'    G—G—C—C—T—A—G—G—C—Cp
```

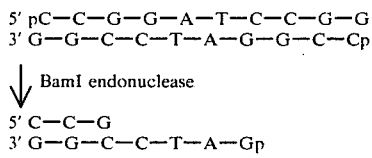

```
5' C—C—G
3' G—G—C—C—T—A—Gp
```

A second method by which duplex adaptor molecules having one protruding nucleotide sequence may be prepared involves the chemical synthesis of a first single-stranded oligonucleotide which includes the recognition site for a restriction endonclease and a second single-stranded oligonucleotide which does not include the recognition site for the restriction endonuclease but is otherwise complementary to the first, that is, one oligonucleotide is longer than the other and the nucleotides which correspond to the recognition site of the restriction endonuclease are protruding. Upon forming a double-stranded duplex from the oligonucleotides, an adaptor molecule results in which the recognition site protrudes.

For example, an oligonucleotide having the sequence 5' pG-A-T-C-C-C-C-G-G-G can be synthesized by the method described previously, and similarly an oligonucleotide having the sequence 5' pC-C-G-G-G can be synthesized. A duplex of these oligonucleotides can be formed as previously described which results in an adaptor molecule having the protruding sequence for BamI restriction endonuclease, namely, 5' pG-A-T-C. This type of adaptor can be defined as a ready-made adaptor. The following is illustrative:

BamI site

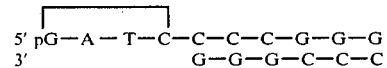

```
5' pG—A—T—C—C—C—C—G—G—G
3'             G—G—G—C—C—C
```

Duplex adaptor molecules having two protruding nucleotide sequences which are recognition sites for the same or different restriction endonucleases can be prepared in a similar way. Single-stranded oligonucleotides which include the recognition site for a restriction endonuclease and are partially complementary are chemically synthesized. A double-stranded duplex is then formed from the oligonucleotides in which the nucleotide sequences which are recognition sites for the same or different restriction endonucleases protrude at opposite ends of the duplex.

Conversion Adaptor Molecules

Duplex conversion adaptor molecules having two protruding nucleotide sequences which are recognition sites for two different restriction endonucleases can be prepared by chemical synthesis of two single-stranded oligonucleotides which are partially complementary. A partially double-stranded duplex is then formed from the oligonucleotides in which the nucleotide sequences which are recognition sites for the two different restriction endonucleases protrude at opposite ends of the duplex. The following example is illustrative:

BamI site

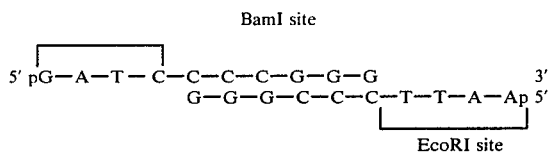

EcoRI site

A conversion adaptor molecule with two different protruding nucleotide sequences can also be made by joining two different even-ended adaptor molecules using polynucleotide ligase, followed by digestion with the two appropriate restriction endonucleases.

A second type of conversion adaptor molecule, a completely single-stranded oligodeoxynucleotide, having two recognition sites for two different restriction endonucleases can be prepared in a similar way. This type of conversion adaptor molecule is used to convert a 3' protruding nucleotide sequence at the termini of a DNA molecule to be cloned to a 5' protruding sequence, or vice versa. For example, HaeII restriction endonuclease digests DNA to give 3' protruding ends, 3' d(C-G-C-G). In order to clone a DNA molecule such as DNA-X with 3' protruding d(C-G-C-G) ends, the conversion adaptor can be joined to each end of DNA-X to produce a DNA molecule containing protruding 5' A-A-T-T ends. The latter can then be joined to the same 5' A-A-T-T ends of the cloning vehicle as follows:

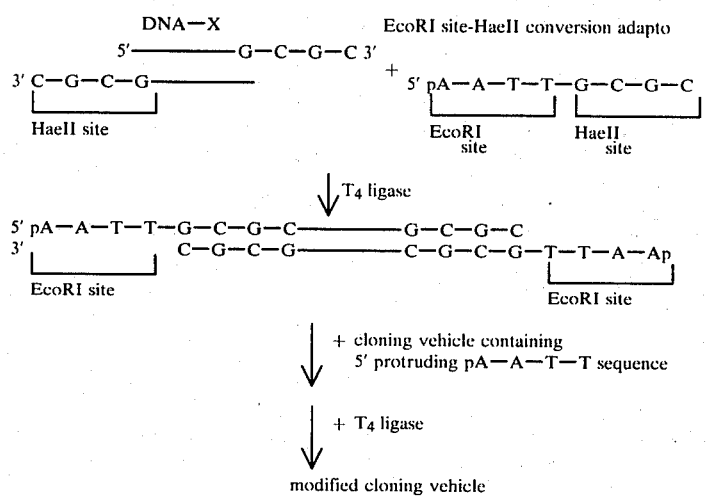

In the event the DNA-X, after cloning, needs to be excised at the EcoRI or HaeII site, then the following conversion adaptor can be used:

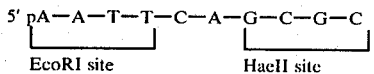

Other examples of such conversion adaptors include: EcoRI site-PstI site, BamI site-HaeII site, BamI site-PstI site, HindIII site-HaeII site, and HindIII site-Pst site.

Adaptor molecules of 3 different lengths can be prepared and used to adjust the genetic informational material, e.g., DNA, which is to be cloned to the proper reading frame for protein synthesis. Once the adaptor molecule is joined to the genetic informational material to be inserted and then inserted into a cloning vehicle and used to transform cells, the expression of the genetic informational material in terms of RNA and protein synthesis depends upon whether the reading frame is correct. In cases where RNA synthesis is initiated from a promoter site on the cloning vehicle, the number of nucleotides between the start of the mRNA and the beginning of the coding sequence of the DNA molecule should be a multiple of 3 in order to keep the reading frame for protein synthesis in phase during the translation of the mRNA sequence into protein sequence. If the exact length of genetic informational DNA is unknown, in order to make the length of genetic informational DNA plus the adaptor as multiples of 3, three different lengths of the adaptor (3n, 3n+1 and 3n+2) must be available. Thus, all of the adaptors discussed must be constructed to give three different lengths. For example, if the adaptor

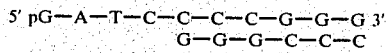

is joined to genetic informational DNA to the cloned, it gives six extra nucleotides (multiple of 3, or 3n+0). The adaptor molecule can be converted to give 3n+1 and 3n+2 as follows:

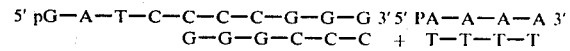

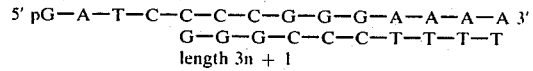

length 3n + 1

If $(pA)_5:(pT)_5$ is used instead of $(pA)_4:(pT)_4$, then after joining it to the adaptor the duplex length will be 3n+2.

In all the adaptors designed so far, the DNA sequence which corresponds to the termination codon for protein synthesis (UAA, UAG, UGA) is avoided.

Adapted DNA Molecules

Adapted DNA molecules can be prepared which include genetic informational material, e.g., DNA, typically in the form of a double-stranded duplex, which is to be inserted into a cloning vehicle and adaptor molecules joined to the ends of the genetic informational material. The genetic informational material can, within the limits imposed by the genetic code, be translated into any polypeptide. It can be naturally derived or synthetically produced.

The adaptor molecules described previously can be joined to opposite ends of genetic informational material which is to be inserted into a cloning vehicle using a polynucleotide ligase, e.g., $T_4$ polynucleotide ligase or E. coli polynucleotide ligase. The adaptor molecules can be identical or different and can have one or two protruding nucleotide sequences depending upon the nature and structure of the genetic informational material such as DNA to which they are joined. The adaptor molecules are extremely useful tools in molecular cloning since the same oligonucleotide adaptor molecules can serve to introduce any double-stranded DNA molecule into cloning vehicles at specific sites. The double-stranded DNA may be obtained by cleavage with a number of restriction endonucleases such as HaeIII and AluI to give even-ended DNA, or the duplex DNA may be chemically synthesized.

Alternatively adapted DNA molecules can be prepared by chemically synthesizing a first single-stranded oligonucleotide which includes the genetic informational material to be inserted into a cloning vehicle and a recognition site for a restriction endonuclease and a second single-stranded oligonucleotide which is partially complementary to the first oligonucleotide and includes a recognition site for a restriction endonuclease, either the same or a different endonuclease. A double-stranded duplex is then formed from the oligonucleotides in which the recognition sites protrude.

Still another method exists for preparing adapted DNA molecules. This involves chemically synthesizing self-complementary single-stranded oligonucleotides which include the recognition site for a restriction endonuclease. Double-stranded duplexes are then formed from pairs of self-complementary oligonucleotides. The duplexes which are formed can be either identical or different. They are enzymatically joined to opposite ends of the genetic informational material to be inserted into a cloning vehicle using a polynucleotide ligase. The resulting molecule is then digested with one or two restriction endonucleases depending upon whether the recognition sites included in the duplexes were for identical or different restriction endonucleases.

To illustrate this method of preparing an adapted DNA molecule, the 21 nucleotide-long lac operator duplex was chemically synthesized. Two oligonucleotide duplexes were separately synthesized which contained the recognition site for a restriction endonuclease, in this case the site for BamI endonuclease. The latter duplexes were then joined to opposite ends of the lac operator using a polynucleotide ligase such as $T_4$ ligase. The resulting molecule was then digested with BamI endonuclease which created protruding recognition sequences for BamI endonuclease, namely, 5′ pG-A-T-C. The following depicts the reaction sequence:

nuclease was prepared as described previously. The 21 nucleotide-long synthetic lac operator was prepared. [Bahl, C. P. et al., PNAS 73, 91 (1976)]. Then the synthetic duplex (about 10 pmole) and the synthetic lac operator (about 1.0 pmole) were joined end-to-end [Sgaramella, V. et al., PNAS 67, 1468 (1970)] by incubating with about 3 units of $T_4$ DNA ligase in about 50 μl of a solution containing about 20 mM Tris-HCl (pH 7.5), about 10 mM dithiothreitol, about 10 mM $MgCl_2$ and about 35 μM ATP at about 20° C. for about 6 hours. The solution was heated to about 70° C. for about 5 minutes to inactivate the ligase and cooled slowly to room temperature, 2 volumes of ethanol were added, and after about 12 hours at about −20° C. the DNA was pelleted at about 10,000 g for about 1 hour. The pellet was dissolved in about 50 μl of a solution containing about 6.6 mM Tris-HCl (pH 7.5), about 6.6 mM $MgCL_2$ and about 1 mM dithiothreitol. To this solution was added 2 units of BamI endonuclease. The sample was incubated at about 37° C. for about 12 hours to produce the adapted DNA molecule.

Modified Cloning Vehicles

Modified cloning vehicles can be prepared from a cloning vehicle such as plasmid, phage or viral DNA which has been contacted with a restriction endonuclease so that a protruding oligonucleotide complementary to the recognition site for the restriction enzyme has resulted by joining to such an endonuclease-treated cloning vehicle an adapted DNA molecule such as has been described hereinabove. Specific cloning vehicles include pMB9 plasmid DNA ad λ phage DNA. The adapted DNA molecule and the endonuclease-treated cloning vehicle can be enzymatically joined by use of a polynucleotide ligase such as $T_4$ polynucleotide ligase or E. coli. polynucleotide ligase. If the restriction endonuclease site at the termini of the cloning vehicle is

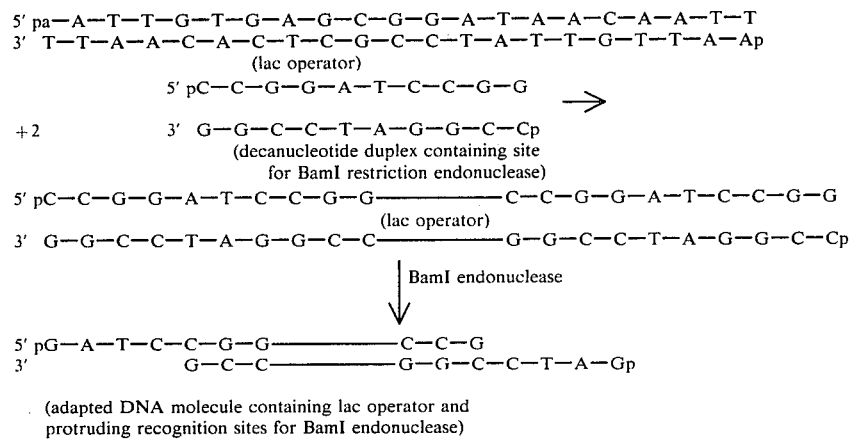

Alternatively, a lac operator DNA has also been synthesized which included the protruding recognition sites for EcoRI endonuclease [Marians, K. J. et al., Nature 263, 744 (1976)]. The lac operator DNA can be joined directly to the DNA to be cloned at the EcoRI site, and then to the cloning vehicle.

To more specifically illustrate, an adapted DNA molecule which included lac operator DNA and protruding nucleotide sequences at both ends which were recognition sites for BamI endonuclease was prepared as follows: First, the synthetic decadeoxyribonucleotide duplex which included the recognition site for BamI endodifferent from that of the DNA molecule to be cloned, either the cloning vehicle or the DNA to be cloned can be modified by the use of adaptors.

By this method, synthetic lac operator DNA has been inserted at the BamI, HindIII and EcoRI sites of pMB9 DNA. For example, linear pMB9 DNA prepared by contacting pMB9 DNA with BamI restriction endonuclease and an adapted DNA molecule which included lac operation DNA and protruding nucleotide sequences at both ends which are recognition sites for BamI endonuclease were heated to about 70° C. for about 5 minutes, cooled slowly to room temperature, and the DNA was precipitated by adding 2 volumes of ethanol and after about 12 hours at about 20° C. the DNA was pelleted at about 10,000 g for about 1 hour. The DNA pellet was dissolved in about 50 μl of a solution containing about 20 mM Tris-HCl (pH 7.5), about 10 mM MgCl$_2$, about 10 mM dithiothreitol and about 35 μM ATP. Three units of DNA ligase were added and the samples were incubated at about 12.5° C. for about 24 hours to produce lac-pMB9 DNA. After heating at about 70° C. for about 5 minutes, and slowly cooling to room temperature, the lac-pMB9 DNA was used directly for transformation as described below.

This method is also suitable for the insertion of multiple copies of a gene such as lac operator DNA into a cloning vehicle or for the insertion of a combination of genes.

In order to characterize the lac-pMB9 DNA, it was isolated after transformation and amplification by the addition of chloramphenicol to the bacterial culture, labelled by nick translation [Maniatis, T. et al, PNAS 72, 1184 (1975)] and then studied for lac repressor binding properties. The inhibitory effect of isopropyl thioglactoside (IPTG) showed that the binding was specific, thus confirming that a lac operator had been inserted into the plasmid.

The modified plasmid DNA was further characterized by digestion with the appropriate restriction endonuclease and then labelled at the 3'-ends by repair synthesis in the presence of [α-$^{32}$P] dNTP [Wu, R. et al., *Methods in Cancer Research* 12, 88 (1976)]. This gave two fragments on polyacrylamide gel electrophoresis which corresponds to the linear pMB9 DNA and to the lac operator.

Transformation

The transfer of genetic informational material such as DNA into host cells, e.g., *E. coli* cells, can be effected by transformation using the modified cloning vehicles. For example, the lac pMB9 DNA was used to transform competent *E. coli* HB 129 cells as follows: The DNA and recipient cells were mixed together and incubated at about 0° C. for about 30 minutes. The temperature of the mixture was raised to about 42° C. for about 2 minutes and then chilled to facilitate uptake of the DNA by the cells. About nine volumes of prewarmed L-broth were added and the cells allowed to recover at about 37° C. for about 2 hours. One volume of L-broth supplemented with about 10 μg ml$^{-1}$ of tetracycline was then added. After an additional approximately 30 minutes at 37° C., the tetracycline concentration was brought up to a final level of about 20 μml$^{-1}$. This cell suspension was used to inoculate 100 ml of M9 medium for the isolation of a larger amount of plasmid DNA [Katz, L. and Helinski, D. R., *J. Bact.* 119, 450 (1973)]. This plasmid DNA (about 30 μg) which contained some modified lac-pMB9 DNA was enriched for lac sequences by binding it to the lac repressor (about 4.5 μg) on a Millipore filter and eluting it with about 1 ml of 1 mM isopropyl thiogalactoside (IPTG). This DNA (about 6% of the input), enriched for lac sequences, was used for a subsequent transformation on nutrient agar plates containing about 20 μg ml$^{-1}$ of tetracycline. The frequency of transformation was $6.4 \times 10^{-4}$ transformants per μg of recombinant DNA per viable cell, whereas in the same conditions native pMB9 gave a frequency of $1.8 \times 10^{-2}$. Since about $1 \times 10^7$ viable cells were used, the number of transformants per μg of recombinant DNA was about 6,000.

Method for Determining Whether Genetic Informational Material Such as DNA Has Been Transferred In order to determine whether genetic informational DNA has been transferred into host cells, an indicator DNA molecule such as the lac operator can be included as part of the genetic informational DNA in an adapted DNA molecule. This adapted DNA molecule is then inserted into a cloning vehicle to prepare a modified cloning vehicle and host cells are transformed using the modified cloning vehicle. If the lac operator is used, transformed cells are screened to determine whether transfer has taken place by plating the trasformed cells in agar plates containing χ-gal which will result in the production of blue colonies if the genetic informational DNA has been transferred because transformed cells which include the lac operator will be constitutive for β-galactosidase synthesis [Miller, J. H., *Experiments in Molecular Genetics,* Cold Spring Harbor Lab. 48 (1972)].

As will be obvious to one skilled in the art, many modifications in the invention are possible without departing from the spirit and scope thereof.

We claim:

1. An adaptor molecule useful for attaching DNA containing genetic information to a cloning vehicle consisting of DNA which comprises a double-stranded oligodeoxyribonucleotide having at one end thereof a protruding nucleotide sequence which is the recognition site for a restriction endonuclease.

2. The adaptor molecule of claim 1 wherein the protruding nucleotide sequence is a part of the recognition site for EcoRI endonuclease.

3. The adaptor molecule of claim 1 wherein the protruding nucleotide sequence is a part of the recognition site for BamI endonuclease.

4. The adaptor molecule of claim 1 wherein the protruding nucleotide sequence is a part of the recognition site for HindIII endonuclease.

5. The adaptor molecule of claim 1 wherein the protruding nucleotide sequence is a part of the recognition site for PstI endonuclease.

6. The adaptor molecule of claim 1 wherein the protruding nucleotide sequence is a part of the recognition site for SalI endonuclease.

7. The adaptor molecule of claim 1 wherein the protruding nucleotide sequence is a part of the recognition site for HaeII endonuclease.

8. The adaptor molecule of claim 1 wherein the protruding nucleotide sequence is a part of the recognition site for XmaI endonuclease.

9. The adaptor molecule of claim 1 wherein the protruding nucleotide sequence is a part of the recognition site for BglII endonuclease.

10. An adaptor molecule useful for attaching DNA containing genetic information to a cloning vehicle consisting of DNA which comprises a double-stranded oligodeoxyribonucleotide having at opposite ends thereof first and second protruding nucleotide sequences which are recognition sites for restriction endonucleases.

11. The adaptor molecule of claim 10 wherein said first and second protruding nucleotide sequences are recognition sites for the same restriction endonuclease.

12. The adaptor molecule of claim 10 wherein said first and second protruding nucleotide sequences are recognition sites for different restriction endonucleases.

13. An adaptor molecule useful for attaching DNA containing genetic information to a cloning vehicle consisting of DNA which comprises a single-stranded oligodeoxyribonucleotide having nucleotide sequences which include the recognition sites for two different restriction endonucleases at opposite ends thereof.

14. An adapted DNA molecule which comprises double-stranded DNA containing genetic information to be attached to a cloning vehicle, a first adaptor molecule according to either claim 1 or claim 10 attached to one end of said DNA and a second adaptor molecule according to either claim 1 or claim 10 attached to the other end.

15. An adaptor molecule of claim 1 having the structure:

5' C—C—G

3' G—G—C—C—T—A—Gp

16. An adaptor molecule of claim 1 having the structure:

5' pG—A—T—C—C—C—C—G—G—G
3'                G—G—G—C—C—C

17. An adaptor molecule of claim 10 having the structure:

5' pG—A—T—C—C—C—C—G—G—G                3'
                 G—G—G—C—C—C—T—T—A—Ap 5'

18. An adaptor molecule of claim 13 having the structure:

5' pA—A—T—T—C—A—G—C—G—C

19. An adaptor molecule of claim 1 containing up to about sixteen deoxyribonucleotides.

* * * * *